United States Patent
Ohishi

(10) Patent No.: US 9,433,392 B2
(45) Date of Patent: Sep. 6, 2016

(54) MEDICAL IMAGE PROCESSING APPARATUS, X-RAY DIAGNOSTIC APPARATUS, AND MEDICAL IMAGE PROCESSING METHOD

(71) Applicants: Kabushiki Kaisha Toshiba, Minato-ku (JP); Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 82 days.

(21) Appl. No.: 14/551,253

(22) Filed: Nov. 24, 2014

(65) Prior Publication Data

US 2015/0150526 A1 Jun. 4, 2015

(30) Foreign Application Priority Data

Nov. 29, 2013 (JP) .................. 2013-247052

(51) Int. Cl.
*G06K 9/00* (2006.01)
*A61B 6/00* (2006.01)
*G06T 5/50* (2006.01)

(52) U.S. Cl.
CPC .............. *A61B 6/469* (2013.01); *A61B 6/463* (2013.01); *A61B 6/481* (2013.01); *A61B 6/504* (2013.01); *A61B 6/5211* (2013.01); *G06T 5/50* (2013.01); *G06T 2207/10116* (2013.01); *G06T 2207/20224* (2013.01); *G06T 2207/30101* (2013.01); *G06T 2210/41* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,553,619 | A * | 9/1996 | Prince | A61B 5/411 600/420 |
| 6,195,579 | B1 * | 2/2001 | Carroll | G01R 33/561 324/306 |
| 6,259,940 | B1 * | 7/2001 | Bernstein | G01R 33/56308 324/309 |
| 6,535,821 | B2 * | 3/2003 | Wang | A61B 6/481 600/415 |
| 6,603,992 | B1 * | 8/2003 | Debbins | G01R 33/5601 600/413 |
| 7,046,833 | B2 * | 5/2006 | Masumoto | G06T 7/0081 382/131 |
| 7,313,428 | B2 * | 12/2007 | Meaney | A61B 5/055 324/306 |
| 7,467,006 | B2 * | 12/2008 | Abe | G01R 33/5601 324/307 |
| 7,738,626 | B2 * | 6/2010 | Weese | A61B 6/481 378/41 |

(Continued)

*Primary Examiner* — Anand Bhatnagar
(74) *Attorney, Agent, or Firm* — Oblon, McClelland, Maier & Neustadt, L.L.P.

(57) ABSTRACT

According to one embodiment, a medical image processing apparatus includes an image data acquisition part, a range setting part and a blood vessel image generation part. The image data acquisition part receives one of X-ray contrast image and subtraction image, of an imaging region including blood vessels of an object. The subtraction image are generated by subtraction processing between the X-ray contrast image and non-contrast X-ray image. The range setting part sets a target range in the X-ray contrast image or subtraction image. The blood vessel image generation part derives time changes in concentrations of a contrast agent based on the X-ray contrast image or subtraction image, and generates blood vessel image having pixel values corresponding to times, at which concentrations of the contrast agent become a specific condition, within the target range and pixel values corresponding to concentrations of the contrast agent outside the target range.

16 Claims, 10 Drawing Sheets

(56) References Cited

U.S. PATENT DOCUMENTS

| | | | |
|---|---|---|---|
| 8,050,474 B2 | 11/2011 | Baumgart | |
| 8,929,632 B2* | 1/2015 | Horz | A61B 6/481 382/130 |
| 9,019,305 B2* | 4/2015 | Baumgart | A61B 6/463 345/629 |
| 2007/0078333 A1* | 4/2007 | Abe | G01R 33/5601 600/420 |
| 2010/0259550 A1* | 10/2010 | Baumgart | A61B 6/463 345/589 |
| 2013/0028494 A1* | 1/2013 | Groth | G06T 7/0012 382/130 |
| 2013/0077839 A1* | 3/2013 | Horz | G06T 11/001 382/130 |
| 2014/0114185 A1* | 4/2014 | Tolkowsky | A61B 6/507 600/431 |
| 2014/0376791 A1* | 12/2014 | Heigl | G06T 11/008 382/128 |
| 2015/0161790 A1* | 6/2015 | Takahashi | A61B 5/0245 600/424 |
| 2016/0089097 A1* | 3/2016 | Ohishi | A61B 6/5235 378/62 |

* cited by examiner

MEDICAL IMAGE PROCESSING APPARATUS, X-RAY DIAGNOSTIC APPARATUS, AND MEDICAL IMAGE PROCESSING METHOD

CROSS REFERENCES TO RELATED APPLICATIONS

This application is based upon and claims the benefit of priority from Japanese Patent Application No. 2013-247052, filed on Nov. 29, 2013; the entire contents of which are incorporated herein by reference.

Further, the entire contents of Japanese Patent Application No. 2014-193154, filed on Sep. 22, 2014 are incorporated herein by reference.

FIELD

Embodiments described herein relate generally to a medical image processing apparatus, an X-ray diagnostic apparatus, and a medical image processing method.

BACKGROUND

DSA (Digital Subtraction Angiography) is known as one of imaging methods for blood vessels in an X-ray diagnostic apparatus. DSA is the technology to acquire subtraction image data between frames of X-ray image data before and after injecting a contrast agent into an object, for diagnosis. That is, X-ray image data is acquired before injecting a contrast agent as a mask image data for generating subtraction image data. On the other hand, X-ray contrast image data is acquired by injecting the contrast agent. Then, DSA image data is generated for diagnosis by subtraction processing between the X-ray contrast image data and the mask image data.

Such DSA image data can be generated as image data in which unnecessary shades in observation of a blood vessel are removed. That is, diagnostic image data in which blood vessels enhanced by a contrast agent are depicted selectively can be obtained. Consequently, images useful for diagnosis of a blood vessel can be displayed.

An object of the present invention is to provide a medical image processing apparatus, an X-ray diagnostic apparatus, and a medical image processing method which can generate X-ray diagnostic images allowing easy viewing of a target blood vessel even when blood vessels branch intricately.

DETAILED DESCRIPTION

Figure 1:
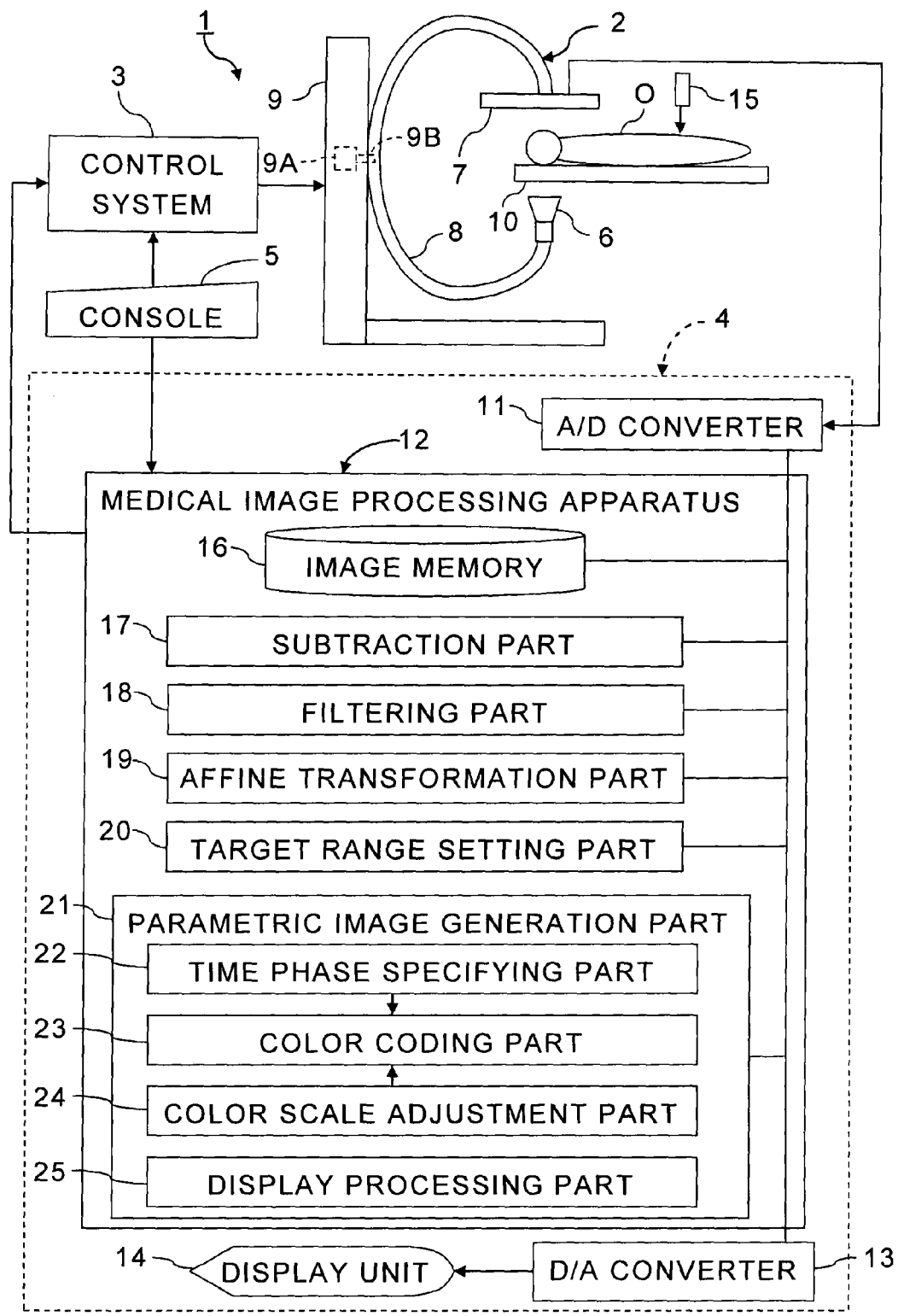
FIG. 1 is a configuration diagram of an X-ray diagnostic apparatus and a medical image processing apparatus according to the first embodiment of the present invention.

In general, according to one embodiment, a medical image processing apparatus includes an image data reception part, a range setting part and a blood vessel image generation part. The image data acquisition part is configured to receive at least one of X-ray contrast image data and subtraction image data, of an imaging region including blood vessels of an object. The subtraction image data are generated by subtraction processing between the X-ray contrast image data and non-contrast X-ray image data. The range setting part is configured to set a target range in the received X-ray contrast image data or the received subtraction image data. The blood vessel image generation part is configured to derive time changes in concentrations of a contrast agent based on the received X-ray contrast image data or the received subtraction image data, and generate blood vessel image data having pixel values corresponding to times, at which concentrations of the contrast agent become a specific condition, within the target range and pixel values corresponding to concentrations of the contrast agent outside the target range.

Further, according to another embodiment, an X-ray diagnostic apparatus includes an imaging system, a range setting part and a blood vessel image generation part. The imaging system is configured to acquire at least X-ray contrast image data of an imaging region including blood vessels of an object. The range setting part is configured to set a target range in the X-ray contrast image data or subtraction image data generated by subtraction processing between the X-ray contrast image data and non-contrast X-ray image data. The blood vessel image generation part is configured to derive time changes in concentrations of a contrast agent based on the X-ray contrast image data or the subtraction image data, and generate blood vessel image data having pixel values corresponding to times, at which concentrations of the contrast agent become a specific condition, within the target range and pixel values corresponding to concentrations of the contrast agent outside the target range.

Further, according to another embodiment, a medical image processing method includes: receiving at least one of X-ray contrast image data and subtraction image data, of an imaging region including blood vessels of an object; setting a target range in the received X-ray contrast image data or the received subtraction image data; and deriving time changes in concentrations of a contrast agent based on the received X-ray contrast image data or the received subtraction image data, and generating blood vessel image data having pixel values corresponding to times, at which concentrations of the contrast agent become a specific condition, within the target range and pixel values corresponding to concentrations of the contrast agent outside the target range. The subtraction image data are generated by subtraction processing between the X-ray contrast image data and non-contrast X-ray image data.

A medical image processing apparatus, an X-ray diagnostic apparatus, and a medical image processing method according to embodiments of the present invention will be described with reference to the accompanying drawings.

First Embodiment

FIG. 1 is a configuration diagram of an X-ray diagnostic apparatus and a medical image processing apparatus according to the first embodiment of the present invention.

An X-ray diagnostic apparatus 1 includes an imaging system 2, a control system 3, a data processing system 4 and a console 5. The imaging system 2 has an X-ray tube 6, an X-ray detector 7, a C-shaped arm 8, a base 9 and a bed 10. In addition, the data processing system 4 has an A/D (analog to digital) converter 11, a medical image processing apparatus 12, a D/A (digital to analog) converter 13, and a display unit 14. Note that, the A/D converter 11 may be integrated with the X-ray detector 7.

The X-ray tube 6 and the X-ray detector 7 are settled at both ends of the C-shaped arm 8 so as to be mutually opposed at both side of the interjacent bed 10. The C-shaped arm 8 is supported by the base 9. The base 9 has a motor 9A and a rotation mechanism 9B. The motor 9A and the rotation mechanism 9B drive so as to rotate the X-ray tube 6 and the X-ray detector 7 fast into a desired position together with the C-shaped arm 8 like a propeller.

As the X-ray detector 7, a FPD (flat panel detector) or I.I.-TV (image intensifier TV) can be used. Furthermore, the output side of the X-ray detector 7 is connected with the A/D converter 11 of the data processing system 4.

The control system 3 drives and controls the imaging system 2 by outputting control signals to the respective elements consisting of the imaging system 2. The control system 3 is connected with the console 5 as an input device. Therefore, instruction of imaging conditions and the like to the control system 3 can be input from the console 5.

Then, the imaging system 2 is configured to expose X-rays toward an object O set on the bed 10 at mutually different angles sequentially from the rotatable X-ray tube 6 under control by the control system 3. In addition, the imaging system 2 is configured to acquire X-rays transmitting the object O from the plural directions sequentially as X-ray projection data by the X-ray detector 7. The X-ray projection data acquired by the X-ray detector 7 are output to the A/D converter 11 as X-ray image data.

Furthermore, a contrast agent injector 15 is provided in the vicinity of the object O set on the bed 10 in order to inject a contrast agent into the object O. Thus, X-ray contrast imaging of an object O can be performed by injecting a contrast agent from the contrast agent injector 15 into a blood vessel of the object O. Thereby, the imaging system 2 has a function to acquire at least X-ray contrast image data of an imaging region, including blood vessels, of an object O. Of course, the imaging system 2 also has a function to acquire non-contrast X-ray fluoroscopic image data. Moreover, the contrast agent injector 15 can be also controlled by the control system 3.

Next, configurations and functions of the medical image processing apparatus 12 will be described.

The input side of the medical image processing apparatus 12 is connected with the output side of the A/D converter 11. Meanwhile, the display unit 14 is connected to the output side of the medical image processing apparatus 12 through the D/A converter 13. Moreover, the medical image processing apparatus 12 is connected with the console 5. Then, direction information required for data processing can be input into the medical image processing apparatus 12 by operation of the console 5.

Note that, aside from the medical image processing apparatus 12 built in the X-ray diagnostic apparatus 1 as illustrated in FIG. 1, a similar medical image processing apparatus as an independent system may be connected with the X-ray diagnostic apparatus 1 through a network. When an independent medical image processing apparatus is connected with the X-ray diagnostic apparatus 1, the medical image processing apparatus includes an image data reception part which receives necessary X-ray image data from the X-ray diagnostic apparatus 1. On the other hand, when the medical image processing apparatus 12 is built in the X-ray diagnostic apparatus 1, the medical image processing apparatus 12 has a function as an image data reception part which receives X-ray image data acquired by the imaging system 2.

The medical image processing apparatus 12 includes an image memory 16, a subtraction part 17, a filtering part 18, an affine transformation part 19, a target range setting part 20, and a parametric image generation part 21. The parametric image generation part 21 has a time phase specifying part 22, a color coding part 23, a color scale adjustment part 24, and a display processing part 25.

The medical image processing apparatus 12 having such functions can be configured by a computer reading a medical image processing program. The medical image processing program can be recorded on an information recording medium to be distributed as a program product so that a general purpose computer can be used as the medical image processing apparatus 12. However, circuits may be used to configure the medical image processing apparatus 12.

The image memory 16 is a storage unit for storing X-ray image data acquired by the imaging system 2. Therefore, when non-contrast X-ray imaging has been performed, non-contrast X-ray image data is stored in the image memory 16. Meanwhile, X-ray imaging has been performed with injecting a contrast agent into an object O, X-ray contrast image data is stored in the image memory 16.

The subtraction part 17 has a function to generate time series DSA image data, depicting contrast-enhanced blood vessels, by subtraction processing between non-contrast X-ray image data read from the image memory 16 and time series X-ray contrast image data.

The filtering part 18 has a function to perform desired filter processing, such as a high-frequency accentuation filter, a low pass filter, or a smoothing filter, of arbitrary data.

The affine transformation part 19 has a function to perform affine transformation processing, such as an expansion, a minification, a rotation movement, and a parallel translation, of X-ray image data, according to direction information input from the console 5.

The target range setting part 20 has a function as an image data acquisition part which acquires at least one of time series X-ray contrast image data and time series DSA image data of an imaging region involving blood vessels of an object O and a function to set a focused region in the imaging region of the acquired X-ray contrast image data or DSA image data. The time series X-ray contrast image data can be retrieved from the image memory 16. On the other hand, the time series DSA image data can be retrieved from the subtraction part 17.

A focused region can be manually set as a ROI (region of interest) by operation of the console 5. That is, a region specified by operation of an input device can be set as a focused region.

The parametric image generation part 21 has a function to derive time changes in concentration of a contrast agent based on time series DSA image data or time series X-ray contrast image data and a function to generate parametric image data, having pixel values corresponding to times at which the concentrations of the contrast agent become a specific condition, as blood vessel image data.

Furthermore, the parametric image generation part 21 is configured to derive time changes in concentrations of a contrast agent, in an imaging region or a focused region set in the target range setting part 20, and to generate parametric image data having pixel values corresponding to times when the concentrations of the contrast agent in the focused region become a specific condition.

For that purpose, the time phase specifying part 22 has a function to specify time phases, at which concentrations of the contrast agent become under a specific condition, based on profiles indicating time changes in the concentrations of the contrast agent. Moreover, the color coding part 23 has a function to assign colors corresponding to time phases specified by the time phase specifying part 22. The color scale adjustment part 24 has a function to determine a color scale used for color coding in the color coding part 23.

The specific condition for assigning colors can be determined, according to diagnostic purposes, to concentrations of a contrast agent corresponding to time points when the contrast agent has flowed in or arrived at a focused blood vessel, concentrations of a contrast agent corresponding to time points when the contrast agent has flowed out from a focused blood vessel contrarily, or the like. For example, a time defining the specific condition can be a time when a concentration of a contrast agent becomes the maximum value, a predetermined ratio of the maximum value, or a threshold value.

Figure 2:
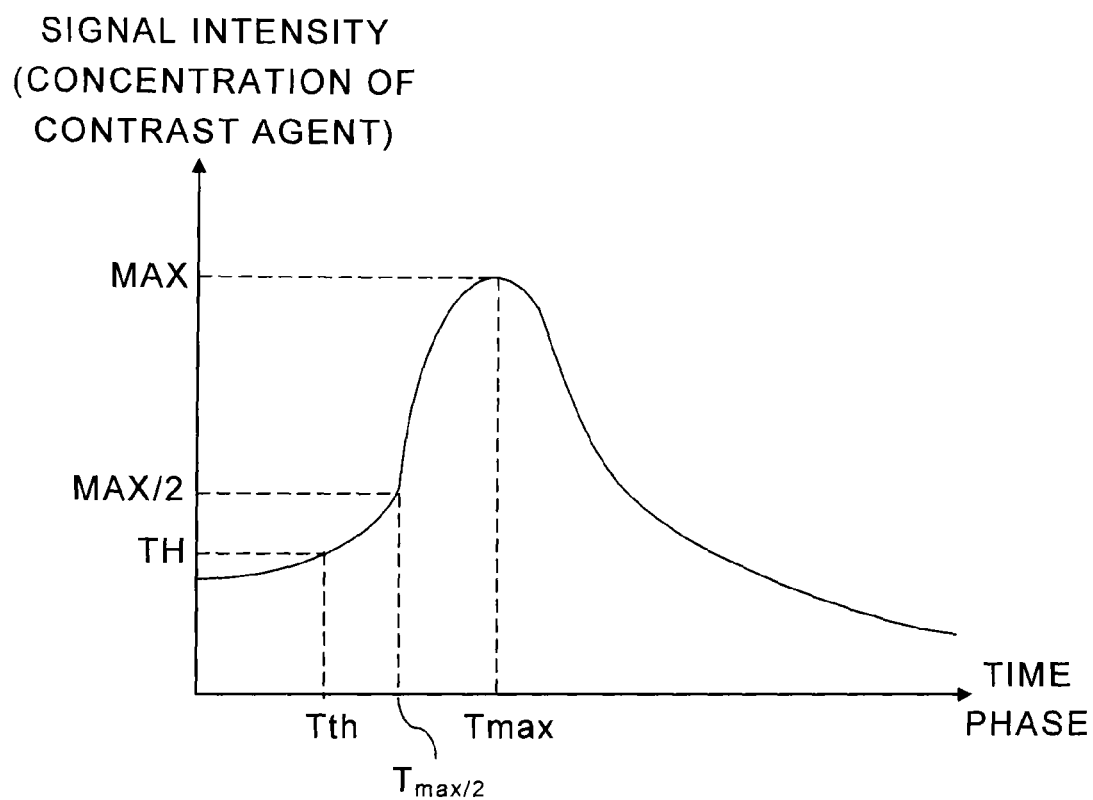
FIG. 2 shows a graph for explaining a method of identifying an inflow time or an arrival time of a contrast agent to a blood vessel based on a concentration profile of the contrast agent.

FIG. 2 shows a graph for explaining a method of identifying an inflow time or an arrival time of a contrast agent to a blood vessel based on a concentration profile of the contrast agent.

In FIG. 2, the horizontal axis shows the time phase direction while the vertical axis shows intensities of image signals, of DSA image data or contrast image data, representing concentrations of a contrast agent. As shown in FIG. 2, a profile in concentration change of the contrast agent can be obtained as a curve, showing signal intensities changing in time, by focusing a pixel corresponding to a blood vessel region of the time series DSA image data or contrast image data.

A typical concentration change profile becomes a curve of which the value increases gradually with the inflow of a contrast agent and decreases gradually with the outflow of the contrast agent. Therefore, when a threshold value TH for detecting a rising up of the curve is set for values of the concentration change profile, it becomes possible to identify a time phase at a start of contrast agent inflow into a focused blood vessel as a time phase Tth when the concentration of the contrast agent has reached the threshold value TH.

However, in a case that noises are large, the time phase at the start of a contrast agent inflow may be identified incorrectly. For this reason, a predetermined ratio within the range of 5% to 10% of the maximum value in a concentration profile of a contrast agent may be used for the threshold value so that influences of noises can be suppressed. Alternatively, a time phase Tmax at which a concentration of a contrast agent has reached the maximum value MAX or a time phase $T_{max/2}$ at which a concentration of a contrast agent has reached 50% of the maximum value MAX may be detected, from a concentration profile, as a time phase when the contrast agent has arrived at a blood vessel, as shown in FIG. 2. Hereinafter, an example case that an arrival time phase of a contrast agent is identified will be mainly described.

When the specification of a time phase, based on a concentration profile of a contrast agent, as shown in FIG. 2, is performed to each required pixel, and colors according to the specified time phases are assigned, parametric image data in which each blood vessel has been depicted in colors according to arrival times of the contrast agent or the like can be generated.

There are some methods for the assignment of colors. For example, a method that red is assigned to the earliest time phase among arrival time phases of a contrast agent while blue is assigned to the latest time phase can be mentioned. In this case, color phases linearly changing from red to blue through green can be assigned to the time phases between the earliest time phase and the latest time phase. Alternatively, a specific period may be set in the time phase change, and a linear change in color phases from red through green and subsequent blue to red may be assigned in the time phase period. Moreover, the assignment processing of linearly changing color phases may also be performed repeatedly and periodically in the time phase direction. A specific example of the method of repeating the assignment processing of color phases in the time phase direction will be mentioned later.

Furthermore, a method of assigning colors so as to display parametric images as a moving image may be adopted. In a case of generating a moving image, a method that a change in color in the time phase direction, assigned as color phases, is moved in the time phase direction along with a progress of playing time can be used. For example, when an arrival time phase T of a contrast agent is displayed in red at a playing time t, what is necessary is to shift a color change in the time direction so that an arrival time phase T+ΔT of the contrast agent is displayed in red at a playing time t+Δt.

Such assignment of colors and temporal alteration of the assigned colors make it possible to display a parametric image so that a specific color moves according to an arrival time phase of contrast agent. Therefore, when a red part is focused, for example, a visual line naturally moves along with a blood flow. As a result, it becomes possible to perceive a blood flow easily.

Note that, when the generation processing of parametric image data is applied to a whole imaging region of an X-ray contrast image, it is useful to perceive blood flows as a whole, in a case of the color coding that linearly assigns the color phases from red to blue through green. However, it may be difficult to perceive a detailed blood flow in a specific part. Moreover, in a case of displaying a parametric image as a moving image, it may also be difficult to easily distinguish a color to which a visual line should be pointed because a color, such as red, to be focused is scattered in several blood vessels.

Accordingly, parametric image data, whose region has been limited to a focused region set in the target range setting part 20, can be generated. Especially, differences in arrival time phase of a contrast agent in a focused region become small enough, compared with a whole imaging time of an X-ray contrast image, even in an example case that the color coding for linearly assigning the color phases from red to blue through green is performed. For this reason, when a color scale is determined according to arrival time phases of a contrast agent in a focused region, the colors can be changed strongly even for a thin blood flow in a specific part. Moreover, a target to which a visual line should be pointed can be easily specified, in a case of displaying a parametric image as a moving image, since a specific color, such as red, to which a visual line should be pointed exists only in a focused region.

When parametric image data in a focused region are generated, subtraction processing for generating DSA image data may be performed to only the focused region. In that case, specification information of the focused region is notified from the target range setting part 20 to the subtraction part 17. Subsequently, in the subtraction part 17, time series DSA image data in which contrast-enhanced blood vessels have been depicted are generated by subtraction processing between non-contrast X-ray image data in the focused region and time series X-ray contrast image data in the focused region.

On the contrary, DSA image data and parametric image data in an imaging region may be generated, and subsequently, a focused region may be set in X-ray contrast image data or the DSA image data using the parametric image data as reference image data.

Moreover, in the generation processing of parametric image data in an imaging region or a focused region, a time change in concentration of a contrast agent at each pixel representative of several pixels may be obtained by moving average processing. That is, a matrix size of image data whose concentration changes of a contrast agent should be obtained can be reduced with smoothing processing. Moreover, concentration changes of a contrast agent may be obtained based on image data whose noises have been removed by low pass filter processing. These processing also can be said as moving average processing and low pass filter processing of concentration profiles of a contrast agent in a spatial direction.

The moving average processing and the low pass filter processing can also be performed in not only spatial directions but also the time direction. In the case that the moving average processing or the low pass filter processing is performed in the time direction, the processing is performed to concentration profiles of a contrast agent in the time direction.

Therefore, parametric image data can be generated based on time changes in concentration of a contrast agent after moving average processing in at least one of the time direction and a spatial direction. Moreover, parametric image data can be generated based on time changes in concentration of a contrast agent after low pass filter processing in at least one of the time direction and a spatial direction. Thereby, smooth parametric image data from which the noises have been removed can be generated.

Moreover, parametric image data can also be generated based on time changes, in concentration of a contrast agent, each having a data interval shorter than a sampling interval of the concentrations of the contrast agent corresponding to an imaging interval of X-ray contrast image data. A time change, of a concentration of a contrast agent, which has a data interval shorter than a sampling interval of the concentration of the contrast agent, can be obtained by arbitrary processing, such as interpolation processing, curve fitting processing using a specific function, or gravity center calculation processing. Thereby, it becomes possible to identify an arrival time of a contrast agent or the like at each pixel with a higher precision. Especially, it is more effective in a case that at least one of moving average processing and low pass filter processing is performed.

By the generation processing of parametric image data as mentioned above, blood vessel image data in which specific time phases, such as arrival time phases of a contrast agent, are displayed in colors can be generated. However, when blood vessels have been branched intricately in an imaging region, it may be difficult to distinguish a target blood vessel. In such a case, it is effective to set a focused region by the target range setting part 20 and to generate parametric image data of the focused region, as mentioned above.

Figure 3:
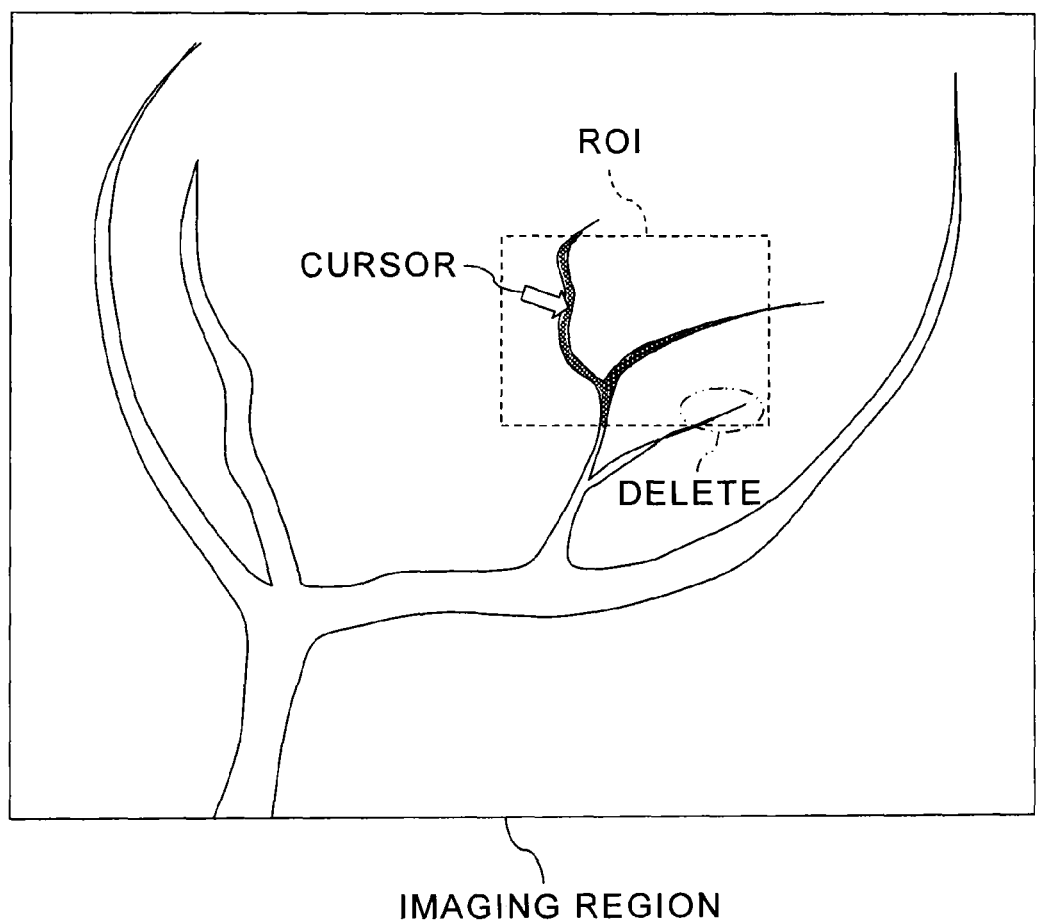
FIG. 3 shows an example of parametric image data generated only for a focused region.

FIG. 3 shows an example of parametric image data generated only for a focused region.

As shown in FIG. 3, a desired ROI including a target blood vessel can be set to a focused region, which is a generation target of parametric image data, in an imaging region corresponding to an image acquisition area of X-ray contrast image data. An X-ray contrast image, a DSA image, or a parametric image of the whole imaging region can be used as a reference image for setting the ROI. When a focused region has been set, a parametric image in which only blood vessels inside the focused region are displayed in colors according to arrival time phases of a contrast agent or the like are generated and displayed, as shown in FIG. 3. For this reason, even in a case that blood vessel s have branched intricately, a target blood vessel can be visually recognized easily.

However, as exemplified in FIG. 3, a blood vessel other than a target blood vessel may be included inside a ROI which is a focused region. In this case, the blood vessel other than the target blood vessel is inconveniently displayed in colors.

Accordingly, a blood vessel at a position, inside a focused region, designated by operation of the console 5 can be tracked. Thereby, a continuous region corresponding to a target blood vessel can be detected. That allows blood vessel regions, which are not connected with the target blood vessel region, to be excluded from the focused region. In this case, the focused region may be updated to the continuous target blood vessel region itself. Alternatively, the focused region from which the blood vessel regions unconnected with the target blood vessel region have been simply excluded may be set as a new focused region.

In the illustrated example, a position on a blood vessel has been designated by a cursor. Therefore, the blood vessel lying on the designated position has been recognized as the target blood vessel, and the continuous target blood vessel region has been extracted. Furthermore, the blood vessel region discontinuous to the target blood vessel region has been excluded from the display target in colors. Thus, isolated blood vessels inside a focused region can be excluded from the display target in colors. For this reason, the target blood vessel can be visually recognized still more easily.

Tracking of a blood vessel can be easily performed by the first threshold processing and the second threshold processing, for example. The first threshold processing is processing of times when concentrations of a contrast agent in a focused region become a specific condition, such as the maximum values. On the other hand, the second threshold processing is processing of differences in times, when concentrations of the contrast agent become a specific condition such as the maximum values, between adjacent pixel positions in the focused region.

Therefore, in a case that parametric image data are generated with assuming that a time at which a concentration of a contrast agent in DSA image data becomes the maximum value is an arrival time of the contrast agent, the first threshold processing and the second threshold processing can be respectively expressed as the formula (1-1) and the formula (1-2) using the first threshold value TH1 and the second threshold value TH2.

$$P(x,y) > TH1 \quad (1\text{-}1)$$

$$\Delta T(x,y) < TH2 \quad (1\text{-}2)$$

In the formula (1-1) and the formula (1-2), P(x, y) is the maximum pixel value of DSA image data at each pixel position (x, y) in a focused region while ΔT(x, y) is a difference in arrival time of a contrast agent, at each pixel position (x, y) in the focused region, between the pixel position (x, y) and at least one adjacent pixel position.

Note that, the adjacent pixel positions whose arrival time difference ΔT(x, y) of a contrast agent should be obtained are limited to pixel positions inside the focused blood vessel region extracted by the first threshold processing using the first threshold value TH1. That is, a blood vessel region that has continuity inside the focused region can be extracted as pixel positions (x, y) which satisfy the simultaneous inequalities expressed by the formula (1-1) and the formula (1-2).

Specifically, blood vessel regions in the focused region can be extracted as positions, at which the pixel values P(x, y) corresponding to the maximum concentrations of a contrast agent exceed the first threshold value TH1, by the first threshold processing shown by the formula (1-1).

On the other hand, by the second threshold processing expressed by the formula (1-2), a continuous blood vessel region can be extracted, from blood vessel regions, as a region in which each of the arrival time differences ΔT(x, y) of the contrast agent between the adjacent pixel positions is less than the second threshold value TH2. That is, the continuity of each blood vessel can be judged by the second threshold processing expressed by the formula (1-2). Moreover, an error, that a noise region having small differences in pixel value between adjacent pixel positions is incorrectly recognized as a continuous blood vessel region, can be avoided by the second threshold processing. Note that, differences in times at which concentrations of the contrast agent become a specific condition can be used as the differences in the arrival times of the contrast agent.

Such a tracking function of a blood vessel and an updating function of a focused region can be provided in the target range setting part 20, for example.

From a viewpoint of improving visibility, it is preferable that a color scale for displaying parametric image data of a focused region is set to be different from one for displaying parametric image data of an imaging region. Accordingly, the color scale adjustment part 24 has a function to generate a color scale corresponding to a range of times when concentrations of a contrast agent in a focused region become a specific condition, such as the maximum values.

Figure 4:
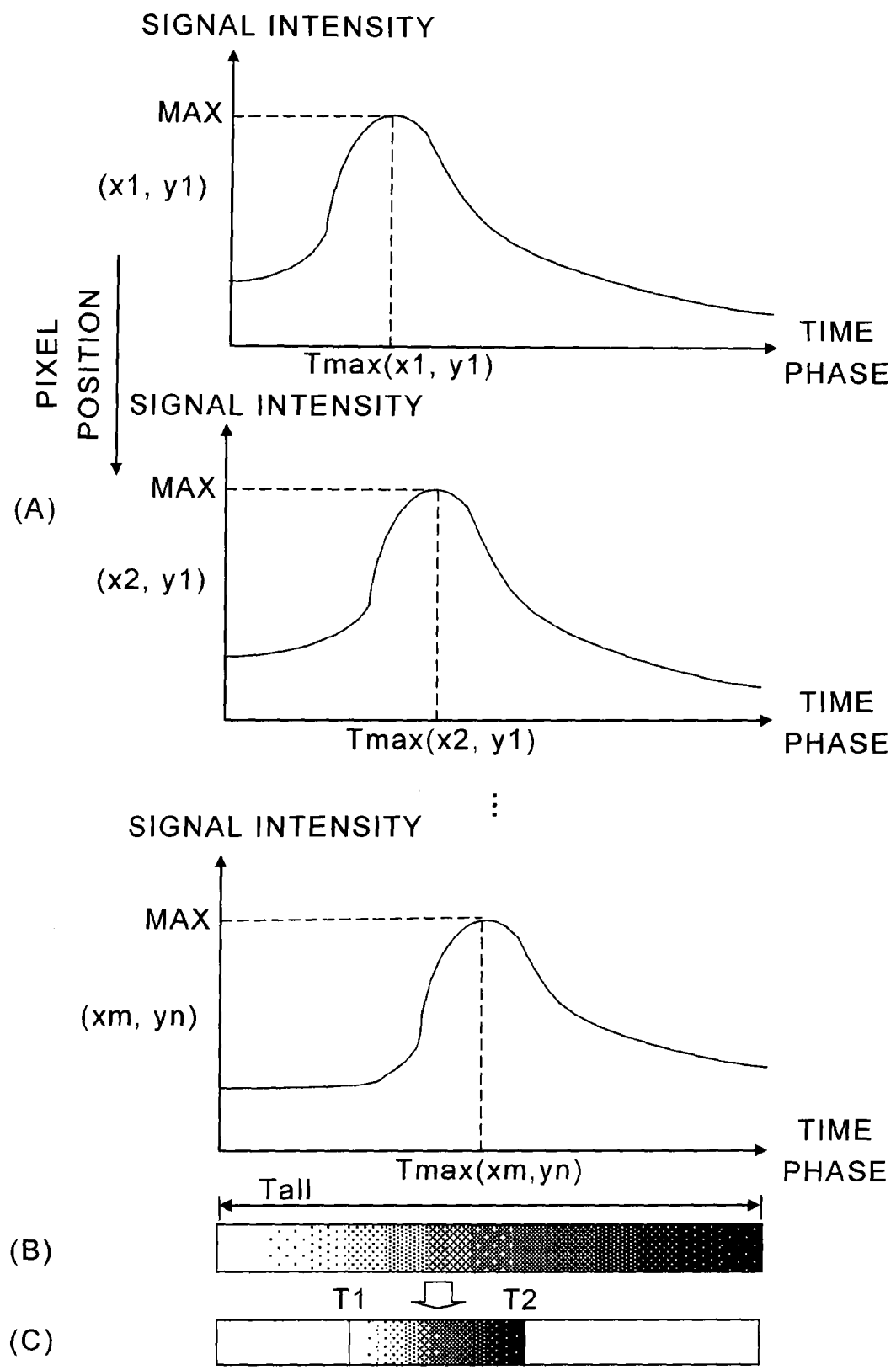
FIG. 4 shows the first example of color scale for displaying parametric image data in a focused region.

FIG. 4 shows the first example of color scale for displaying parametric image data in a focused region.

FIG. 4 (A) shows concentration profiles of a contrast agent at two dimensional positions (xi, yj) (i=1, 2, 3, ..., m; j=1, 2, 3, ..., n) inside a focused region and arrival time phases Tmax(xi, yj) of the contrast agent specified based on the maximum values MAXs of the concentration profiles. The contrast agent arrives in a blood vessel in the upstream side, which is close to an injection position of the contrast agent, relatively early. Therefore, specified time phases are also relatively early. On the other hand, the contrast agent arrives in a blood vessel in the downstream side, which is away from the injection position of the contrast agent, relatively late. Therefore, specified time phases are also relatively late.

FIG. 4 (B) shows an example of color scale in which colors have been assigned so as to correspond all arrival time phases Tall of the contrast agent, which might be specified based on concentration profiles of the contrast agent inside an imaging region. The parametric image data inside the focused region can be generated using the color scale shown in FIG. 4 (B).

However, the range of the time phases specified inside the focused region is more limited than the range of the time phases which might be specified inside the imaging region. Accordingly, a color scale whose colors correspond to the range of the times at which the concentrations of the contrast agent in the focused region become a specific condition can be generated as shown in FIG. 4 (C). Then, parametric image data which have color pixel values can be generated using the color scale corresponding to the focused region.

More specifically, the color scale in which colors have been assigned in a period from a time T1 to a time T2 can be generated as shown in FIG. 4 (C). The time T1 may be the minimum value of the times when the concentrations of the contrast agent in the focused region become a specific condition, such as the maximum values. Alternatively, the T1 may be derived by adding a margin time to the minimum value of the times when the concentrations of the contrast agent in the focused region become a specific condition. On the other hand, the time T2 may be the maximum value of the times when the concentrations of the contrast agent in the focused region become a specific condition, such as the maximum values. Alternatively, the time T2 may be derived by adding a margin time to the maximum value of the times when the concentrations of the contrast agent in the focused region become a specific condition. When the parametric image data of the focused region are generated using such a color scale, a resolution in time phase of the parametric image data can be improved by differences in colors, with covering the range of the time phases inside the focused region.

Note that, a reduction of an initial color scale as shown in FIG. 4 (B), having initial colors corresponding to the range Tall of the times when the concentrations of the contrast agent in the imaging region become a specific condition, in the time direction can also generate a color scale as shown in FIG. 4 (C) in which the colors correspond to the range of the times at which the concentrations of the contrast agent in the focused region become a specific condition. That is, a rate of a color change to a time change in a color scale can be enlarged according to a time range inside a focused region. Thereby, a color scale corresponding to a focused region can be generated by simple processing.

Figure 5:
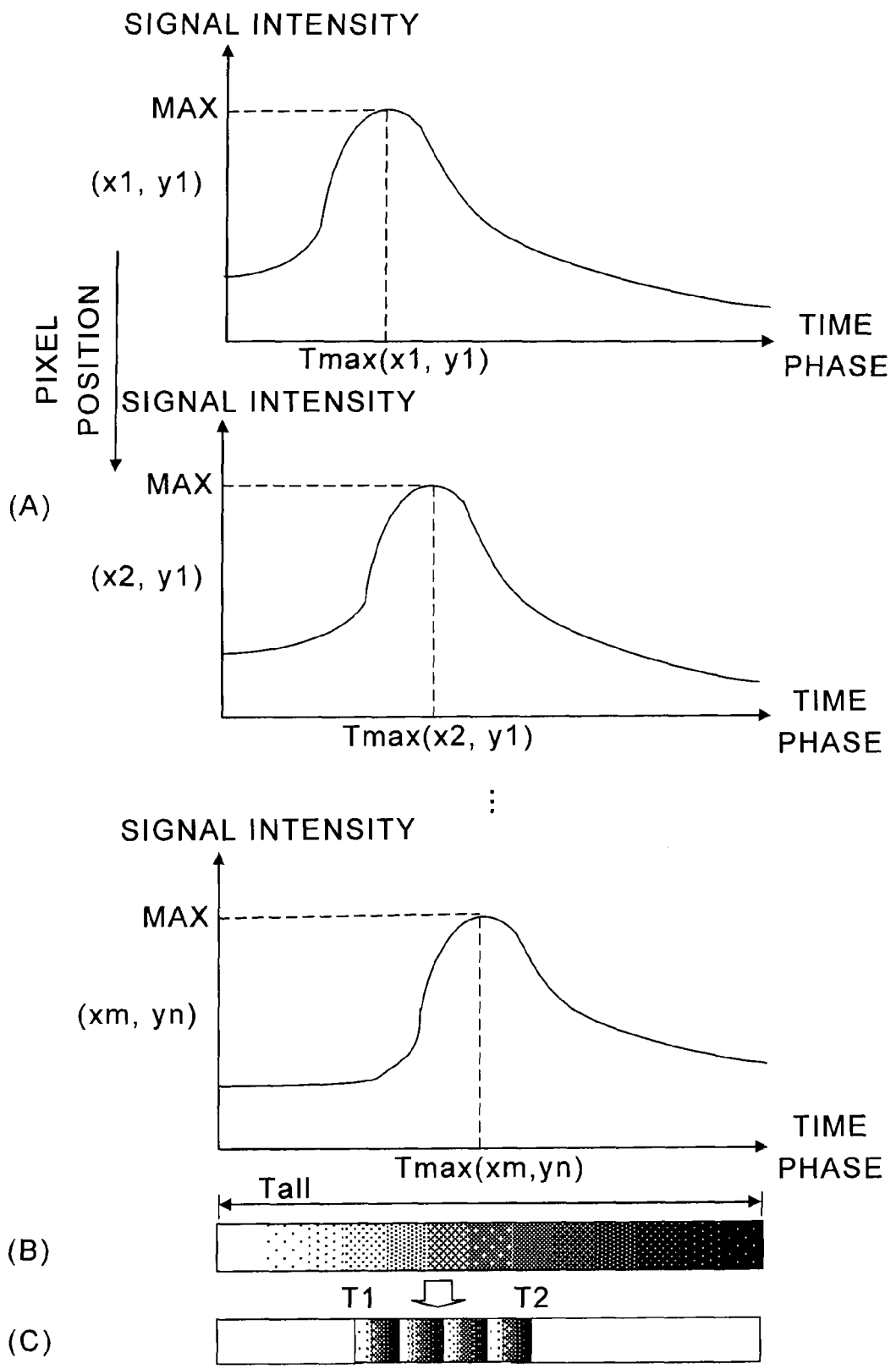
FIG. 5 shows the second example of color scale for displaying parametric image data in a focused region.

FIG. 5 shows the second example of color scale for displaying parametric image data in a focused region.

FIGS. 5 (A) and (B) are similar to FIGS. 4 (A) and (B) respectively. As shown in FIG. 5 (C), a color scale whose change in colors is periodically repeated several times can be generated so that the changes in colors correspond to a range of times when concentrations of a contrast agent in a focused region become a specific condition. That is, a color scale in which a continuous change of color phases is repeated periodically can be generated. In this case, a period, a phase, and an initial phase of the change in colors can be arbitrarily set as conditions for the color scale. When the color scale as shown in FIG. 5 (C) is used, a time resolution by differences in colors can be improved further.

Figure 6:
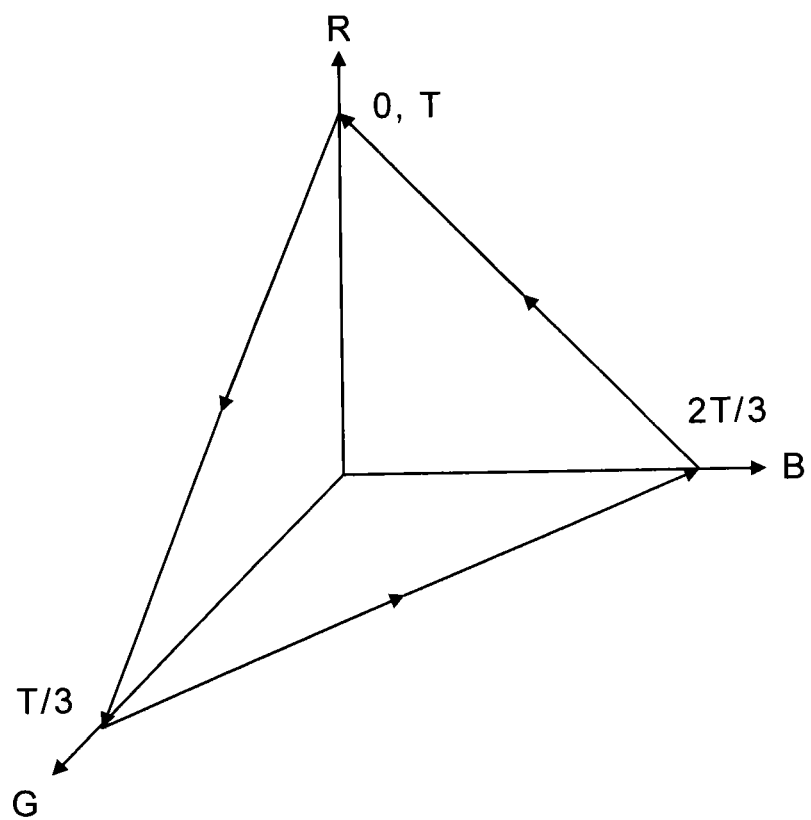
FIG. 6 shows an example of a color scheme in the color scale shown in FIG. 5 (C)

FIG. 6 shows an example of a color scheme in the color scale shown in FIG. 5 (C).

The three orthogonal axes in FIG. 6 represent R values, G values, and B values, respectively. The R value, G value, and B value corresponding to each time phase in one period T of the color phase change can be determined along the sides of the color triangle, whose vertexes are the maximum value of the R values, the maximum value of the G values, and the maximum value of the B values, as shown in FIG. 6. Specifically, the colors can be arranged so that the G value and the B value become zero and the R value becomes the maximum value when the relative time is zero or T, the R value and the B value become zero and the G value becomes the maximum value when the relative time is T/3, and the R value and the G value become zero and the B value becomes the maximum value when the relative time is 2T/3.

When such a color scheme is performed, parametric image data can be generated so that the color changes from red to blue through green, and then returns to red again as the time phase becomes late. Note that, the colors between red, green, and blue can be assigned to time phases so that the R value, the G value, and the B value change linearly, for example. Alternatively, the R values, the G values, and the B values may also be assigned to time phases so that the angle of a line segment, which connects the center of the color triangle with a point on the sides, changes linearly.

When parametric image data are generated according to a color scale generated by such a color scheme, blood vessels can be distinguished as a difference in colors even when differences in arrival times of a contrast agent are small. That is, arrival times of a contrast agent can be understood in detail.

Note that, the color attracting people is red. Therefore, as exemplified in FIG. 6, setting the color of an initial time phase, which corresponds to the earliest arrival time of a contrast agent, to red leads to an improvement of visibility. That is, it is effective to set a color value, corresponding to the initial time phase of a color scale, to the maximum value of the R value. Moreover, as another example, it is also useful to adjust the initial time phase so that a focused time phase becomes red.

Moreover, the color scales exemplified in FIG. 4 and FIG. 5 can also be changed dynamically, as mentioned above. Specifically, a color scale can be generated so that colors, corresponding to a range of times when concentrations of a contrast agent in a focused region become a specific condition such as the maximum values, change in terms of time. Then, parametric image data can be generated as a moving image whose colors change temporally according to the color scale. In this case, parametric image data whose colors move as blood flows can be generated. Consequently, it becomes possible to recognize how blood flows easily.

Note that, arbitrary image data can be displayed in the region, outside a focused region, in an imaging region. For example, parametric image data in a focused region can be combined with DSA image data or X-ray contrast image data, at an arbitrary time phase, of the whole imaging region, for displaying. In this case, the parametric image generation part 21 generates blood vessel image data whose inside of the focused region has pixel values corresponding to times when concentrations of a contrast agent become a specific condition such as the maximum values while outside of the focused region has pixel values corresponding to concentrations of the contrast agent. That is, blood vessel image data whose inside of the focused region is parametric image data and outside of the focused region is DSA image data or X-ray contrast image data at a certain time phase are generated.

Alternatively, parametric image data inside a focused region and X-ray contrast image data or DSA image data inside an imaging region may also be displayed in parallel as frames of blood vessel image data. In this case, the first blood vessel image data, inside the focused region, which have pixel values corresponding to times when concentrations of a contrast agent become a specific condition and the second blood vessel image data, inside the imaging region, which have pixel values corresponding to concentrations of the contrast agent are separately generated so as to be displayed in parallel.

Moreover, parametric image data inside a focused region can be overlapped with desired image data to be displayed. Therefore, the parametric image generation part 21 also has a function to generate image data displayed together with parametric image data.

The display processing part 25 has a function to perform display processing that compounds parametric image data inside a focused region with other image data, as mentioned above. More specifically, the display processing part 25 has a function to perform image composition processing in accordance with designated display conditions. The image composition processing performed by the display processing part 25 is one or both of processing of overlapping parametric image data inside a focused region with corresponding X-ray contrast image data, DSA image data, or the like, for display them and processing of combining parametric image data inside a focused region with X-ray contrast image data, DSA image data, or the like, outside the focused region, for display them.

Next, an operation and an action of the X-ray diagnostic apparatus 1 and the medical image processing apparatus 12 will be described.

Figure 7:
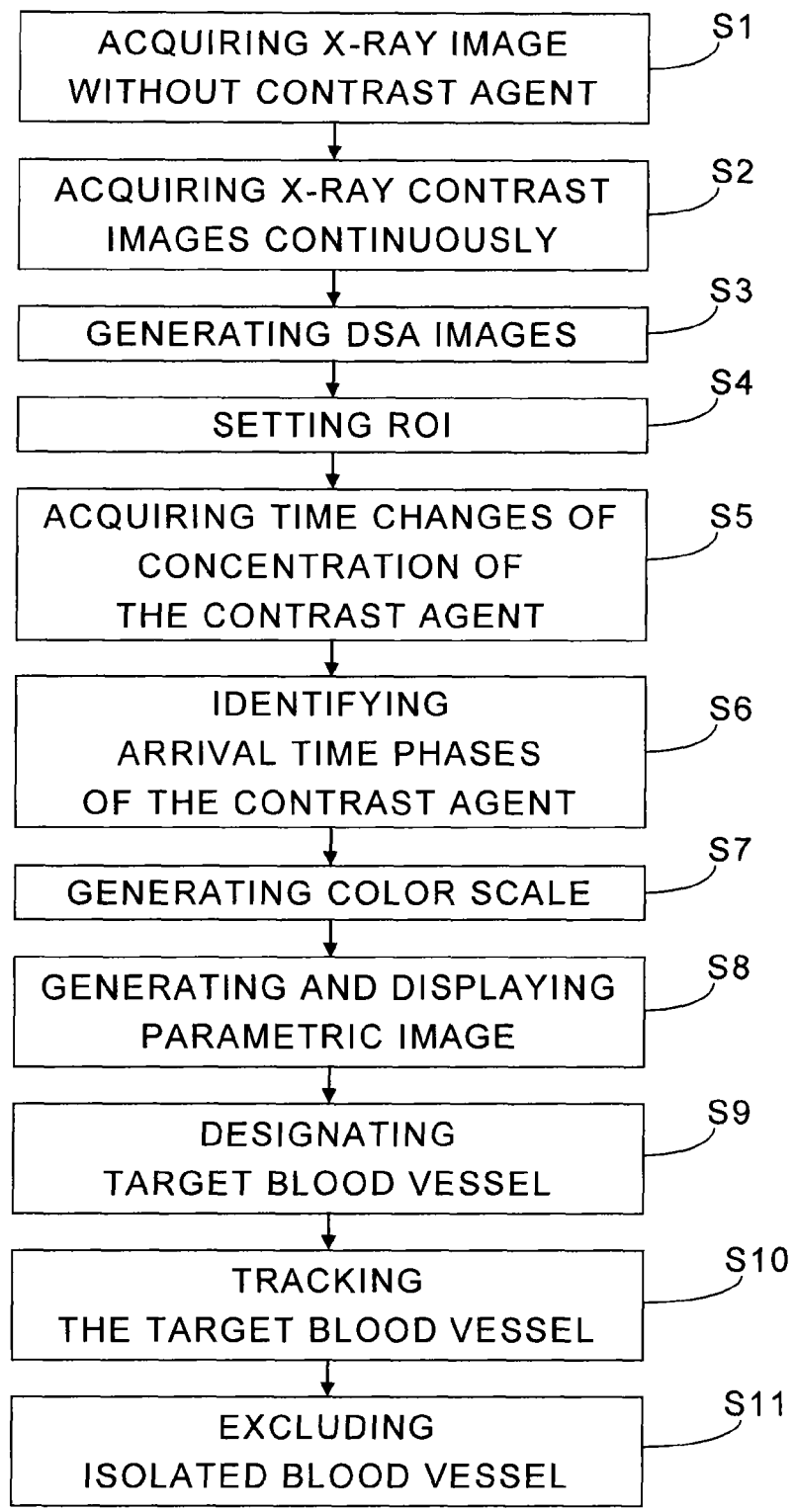
FIG. 7 is a flow chart which shows an operation of the X-ray diagnostic apparatus shown in FIG. 1 and processing in the medical image processing apparatus.

FIG. 7 is a flow chart which shows an operation of the X-ray diagnostic apparatus 1 shown in FIG. 1 and processing in the medical image processing apparatus 12.

First, in Step S1, X-ray image data are acquired without a contrast agent. Specifically, the imaging system 2 moves to a predetermined position and an X-ray is exposed from the X-ray tube 6 towards an object O set on the bed 10, under control by the control system 3. Then, the X-ray which has transmitted the object O is acquired as X-ray projection data by the X-ray detector 7. The X-ray projection data acquired by the X-ray detector 7 are output as X-ray image data to the medical image processing apparatus 12 through the A/D converter 11.

The X-ray image data may be acquired for one frame or multiple frames. When multiple frames of the X-ray image data are acquired and the addition average of the multiple frames of the X-ray image data is calculated in the filtering part 18, one frame of non-contrast X-ray image data whose noises have been reduced can be generated. Subsequently, the non-contrast X-ray image data acquired as mentioned above are stored in the image memory 16.

Next, in Step S2, X-ray contrast image data are acquired continuously. For that purpose, the contrast agent injector 15 operates under a control by the control system 3, and a contrast agent is injected into the object O. Subsequently, after a preset time has passed from the start time of the contrast agent injection, the acquisition of the X-ray contrast image data starts. Then, the acquisition of the X-ray contrast image data is performed continuously in a predetermined period. Thereby, the time series X-ray contrast image data are stored sequentially in the image memory 16.

When the X-ray contrast imaging has been completed, a focused region that includes a target blood vessel is set in the imaging region of the X-ray contrast image data by operations of the console 5 in Step S3. As a user interface for that, the target range setting part 20 displays one representative frame or time series multiple frames of the X-ray contrast image data or DSA image data on the display unit 14. In the case that the DSA image data are displayed, the DSA image data are generated by subtraction processing between the non-contrast X-ray image data and the X-ray contrast image data in the subtraction part 17.

Thereby, a ROI including the target blood vessel can be set using an X-ray contrast image or a DSA image as a reference image as shown in FIG. 3. Then, the medical image processing apparatus 12 starts processing for generating parametric image data with setting the ROI to the focused region. Here, a case that DSA image data are generated only for a focused region and parametric image data are generated based on the generated DSA image data of the focused region will be described as an example.

In that case, in Step S4, the DSA image data of the focused region are generated by the subtraction part 17. More specifically, the time series DSA image data of the focused region are generated sequentially by subtraction processing of the time series X-ray contrast image data of the focused region using the non-contrast X-ray image data of the focused region as mask image data.

Next, in Step S5, time changes in concentrations of the contrast agent inside the focused region are gotten by the time phase specifying part 22. Specifically, the time series DSA image data of the focused region in a time phase period designated by operations of the console 5 are taken into the time phase specifying part 22. Then, a concentration profile showing a time change in concentration of the contrast agent as shown in FIG. 4 (A) or FIG. 5 (A) is generated for every pixel position in the time phase specifying part 22.

Note that, the filtering part 18 can perform one or both of low pass filter processing and moving average processing in one or both of a spatial direction and the time direction, as preprocessing or postprocessing of the generation of the concentration profiles of the contrast agent. Thereby, smooth concentration profiles, of the contrast agent, having reduced noises can be generated. In addition, concentration profiles of the contrast agent whose data intervals are shorter than sampling intervals can also be generated by interpolation processing, gravity center calculation, or curve fitting in the time phase specifying part 22.

Next, in Step S6, arrival time phases of the contrast agent at the respective pixel positions inside the focused region are identified, by the time phase specifying part 22, based on the concentration profiles of the contrast agent. Specifically, the arrival time phase of the contrast agent can be identified for every pixel position inside the focused region by data processing, such as peak detection processing or threshold value processing, of the concentration profiles of the contrast agent.

Note that, after the time phases have been specified by the data processing such as peak detection processing or threshold value processing, continuous concentration profiles only in periods close to the specified time phases may be derived by interpolation processing, gravity center calculation, or curve fitting. In that case, the true arrival time phases of the contrast agent are detected by data processing, such as peak detection processing or threshold value processing, of the derived continuous concentration profiles, for the second time.

Next, in Step S7, the color scale adjustment part 24 generates a color scale for color coding of a two dimensional map of the arrival time phases of the contrast agent acquired by the time phase specifying part 22. The color scale adjustment part 24 can generate not only a color scale corresponding to a range of possible time phases in the imaging region as shown in FIG. 4 (B) or FIG. 5 (B) but also a color scale whose change rate in color phase has been increased so as to correspond to a range of the time phases in the focused region as shown in FIG. 4 (C) or FIG. 5 (C).

In a case that the time phases in the focused region are related to the colors one-on-one as shown in FIG. 4 (C), a color scale can be generated by assigning the colors to the respective time phases between the minimum and the maximum values of the specified time phases inside the focused region. On the other hand, in a case that a color scale whose color phases change repeatedly, continuously and periodically is generated as shown in FIG. 5 (C), conditions including a period and an initial phase of the color phase change are set by operations of the console 5.

Furthermore, a color scale whose colors are temporally changed can also be generated. In that case, conditions, such as a changing rate of the colors, are set.

Next, in Step S8, the color coding part 23 performs color coding, of the two dimensional map of the arrival time phases of the contrast agent, based on the color scale generated by the color scale adjustment part 24. However, the color coding is performed only to the focused region. Specifically, an R value, a G value, and a B value corresponding to an arrival time phase of the contrast agent are assigned to each pixel inside the focused region, as pixel values, according to the color scale. Thereby, parametric image data of the focused region are generated. The generated parametric image can be displayed on the display unit 14. As a result, the parametric image, in which only blood vessels in the focused region are displayed in colors as shown in FIG. 3, is displayed on the display unit 14.

However, blood vessels, that are not of interest, inside the ROI are occasionally displayed in colors, as exemplified in FIG. 3. Accordingly, isolated blood vessels, that are not of interest, inside the ROI can be excluded from targets to be displayed in colors.

In that case, the target blood vessel is designated by operations of the console 5 in Step S9. Specifically, position information on the target blood vessel is input from the console 5 into the target range setting part 20. For example, the target blood vessel can be designated by pointing a cursor on the target blood vessel, as shown in FIG. 3.

Then, in Step S10, the target range setting part 20 performs tracking of the designated target blood vessel. As a result, a connected region of the target blood vessel inside the focused region is specified. On the contrary, each blood vessel, which is not connected with the target blood vessel, is also specified.

Next, in Step S11, the target range setting part 20 excludes blood vessel regions, unconnected with the target blood vessel, from the focused region. As a result, the parametric image is updated together with the focused region and the isolated blood vessels are excluded from the targets to be displayed in colors. Therefore, a user can observe the target blood vessel more easily.

Note that, FIG. 7 shows a flow in case of setting an ROI, for generating and displaying a parametric image, on a DSA image as a reference image. However, a parametric image of a whole imaging region for the DSA image may be generated once so that an ROI can be set on the parametric image of the whole imaging region as a reference image, as mentioned above.

Figure 8:
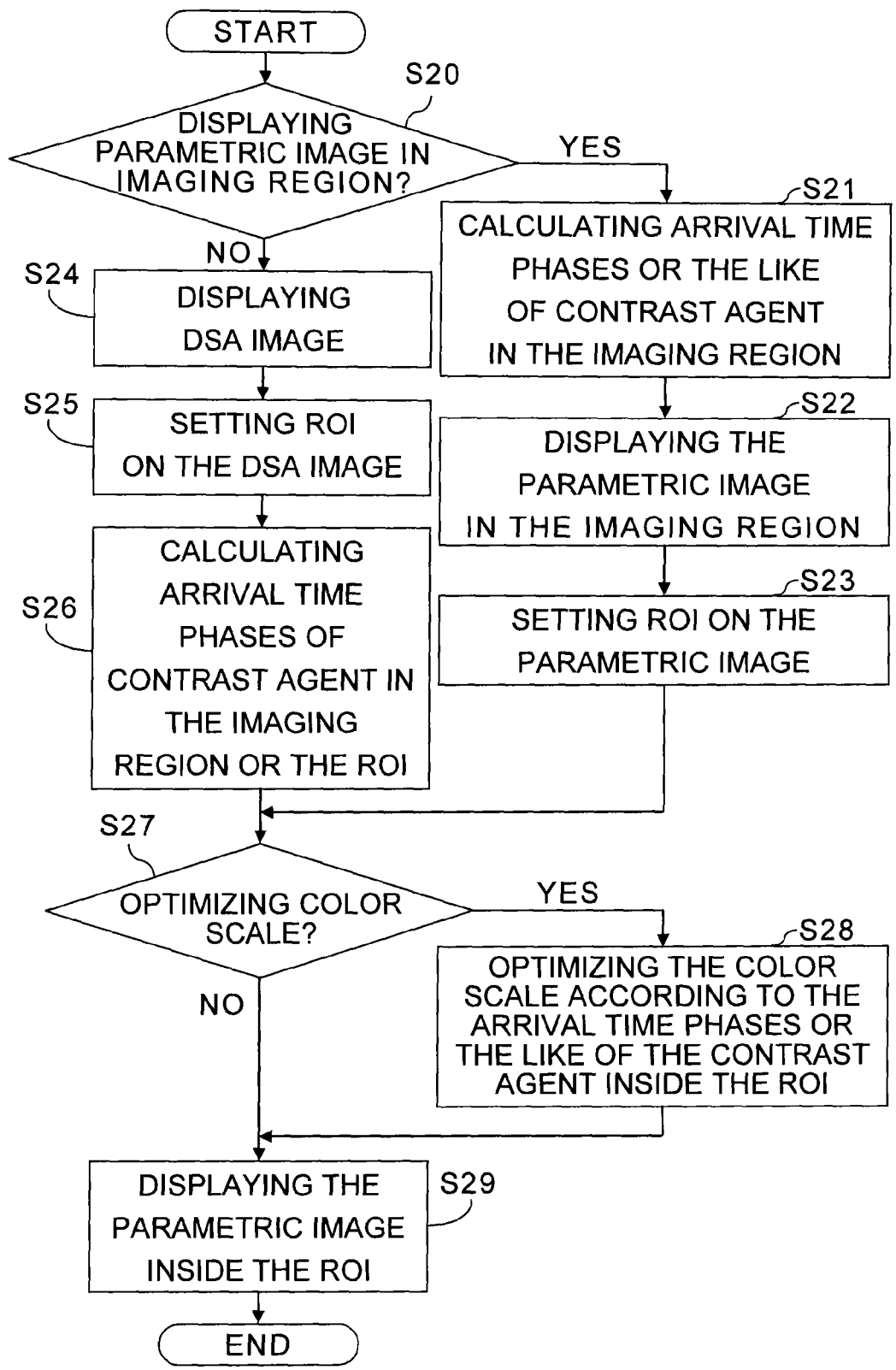
FIG. 8 is a flow chart which shows a variation in flow of data processing in case of generating parametric image data in a focused region.

FIG. 8 is a flow chart which shows a variation in flow of data processing in case of generating parametric image data in a focused region.

At first, in the decision of Step S20, a user can arbitrarily determine whether a parametric image of an imaging region for X-ray contrast imaging is displayed or not. In the case of displaying a parametric image in an imaging region, a time, such as an arrival time phase of a contrast agent, at which a concentration of a contrast agent in the imaging region becomes a specific condition is identified for every pixel position by the time phase specifying part 22, in Step S21. Then, in Step S22, a parametric image in the imaging region can be displayed in colors on the display unit 14 by color coding based on the times identified at the respective pixel positions. Thereby, in Step S23, the user can set an ROI, corresponding to a focused region, inside the imaging region by operations of the console 5 using the parametric image in the imaging region, displayed on the display unit 14, as a reference image.

On the other hand, in the case that a parametric image in the imaging region is not to be displayed, a DSA image in the imaging region is displayed on the display unit 14, in Step S24. Note that, an X-ray contrast image may be displayed instead of a DSA image. Then, in Step S25, the user can set an ROI, corresponding to a focused region, inside the imaging region by operations of the console 5 using a DSA image in the imaging region, displayed on the display unit 14, as a reference image.

When the ROI has been set, a time, such as an arrival time phase of the contrast agent, at which a concentration of the contrast agent inside the imaging region or inside the ROI becomes a specific condition is identified for every pixel position by the time phase specifying part 22 in Step S26. Note that, when the identification of the times is limited inside the ROI, the data processing amount can be reduced. On the other hand, in the case of identifying times when concentrations of the contrast agent in the whole imaging region become a specific condition, the times can also be identified before the setting of an ROI in Step S25.

Next, in the decision of Step S27, the user can arbitrarily determine whether a color scale for color coding of the parametric image data inside the ROI is optimized according to the ROI or not. When the color scale is optimized according to the ROI, a normal color scale as shown in FIG. 4 (B) or FIG. 5 (B) is changed to a color scale, whose change rate in color phase has been increased so as to correspond to a range of the time phases inside the ROI as shows in FIG. 4 (C) or FIG. 5 (C), by the color scale adjustment part 24, in Step S28.

Then, in Step S29, a parametric image inside the ROI is displayed in colors on the display unit 14 by color coding in the color coding part 23 using a color scale as exemplified in FIG. 4 (B), FIG. 4 (C), FIG. 5 (B), or FIG. 5 (C). Thereby, the parametric image limited to inside the ROI can be displayed as blood vessel image data. That is, based on X-ray contrast image data or subtraction image data generated in an injection period of the contrast agent into the object O, blood vessel image data according to time changes of concentrations of the contrast agent in a period when the contrast agent is flowing inside the focused region in the injection period can be generated.

That is, the X-ray diagnostic apparatus 1 and the medical image processing apparatus 12 mentioned above are apparatuses each configured to generate parametric image data only for a focused region. Furthermore, the X-ray diagnostic apparatus 1 and the medical image processing apparatus 12 are apparatuses each configured to generate an appropriate color scale corresponding to a focused region so that arrival time phases of a contrast agent in the focused region can be easily distinguished.

Consequently, according to the X-ray diagnostic apparatus 1 and the medical image processing apparatus 12, a target blood vessel can be traced easily even in a case that blood vessels have branched off intricately. Especially, blood vessel images can also be displayed as a moving image as blood is flowing by temporally changing colors assigned to a color scale. In that case, an uninterested blood vessel might be focused because of a change in colors of the uninterested blood vessel. However, the uninterested blood vessel can be excluded from the targets to be displayed in colors. Therefore, it is possible to concentrate on an observation of blood vessels of interest. This effect is remarkable when a blood flow in a target blood vessel is relatively slow and blood flows in other blood vessels are relatively fast.

Second Embodiment

In the X-ray diagnostic apparatus in the second embodiment, the detailed function of the target range setting part 20 is different from that of the X-ray diagnostic apparatus 1 in the first embodiment. Other configurations and functions of the X-ray diagnostic apparatus in the second embodiment are similar to those in the first embodiment. Therefore, only the detailed function of the target range setting part 20 will be explained.

In the first embodiment, a focused range for which parametric image data are generated is set as a focused region on a reference image, such as a DSA image, in the target range setting part 20. However, a focused time may be set as a focused range. In other words, a focused range for which parametric image data are generated can be specified in terms of time instead of space. Accordingly, the target range setting part 20 in the second embodiment is configured to set a focused range as a focused time range.

Figure 9:
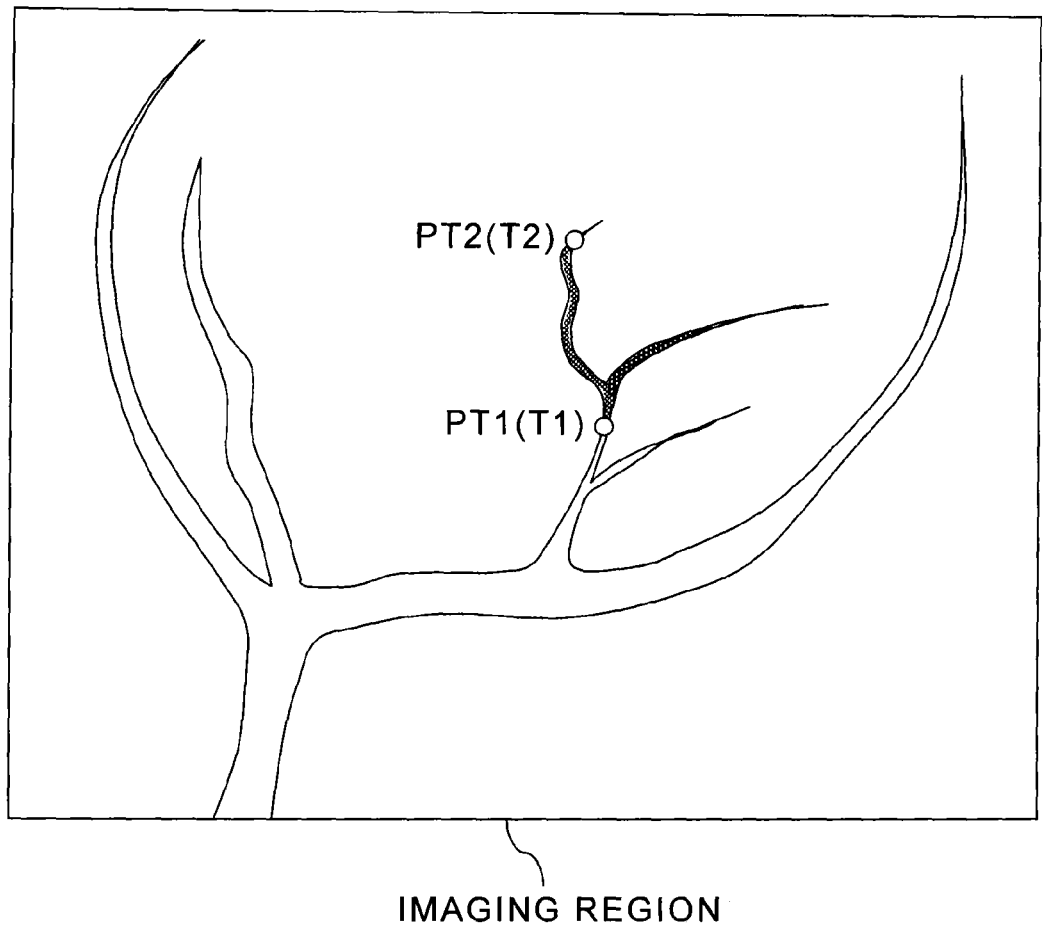
FIG. 9 is a view for explaining the first example of method of setting a focused region, for which parametric image data is generated, in terms of time.

FIG. 9 is a view for explaining the first example of method of setting a focused region, for which parametric image data is generated, in terms of time.

As shown in FIG. 9, a position PT1 in the upstream side of a target blood vessel and a position PT2 in the downstream side can be designated manually by operations of an input device, using an X-ray contrast image, a DSA image, or a parametric image, depicting blood vessels in an imaging region corresponding to an image acquisition region of the X-ray contrast image data, as a reference image. Then, an arrival time phase T1 of a contrast agent at the designated position PT1 in the upstream side and an arrival time phase T2 of the contrast agent at the designated position PT2 in the downstream side can be specified based on time changes of concentrations of the contrast agent at the respective positions PT1 and PT2.

Then, pixel positions, at which arrival time phases of the contrast agent are between the specified first arrival time phase T1 of the contrast agent and the specified second arrival time phase T2 of the contrast agent, can be set as targets of generation processing of parametric image data. Consequently, a parametric image showing only blood vessels, which the contrast agent reached in the period from the first time phase T1 to the second time phase T2, in colors can be generated and displayed as shown in FIG. 9.

Figure 10:
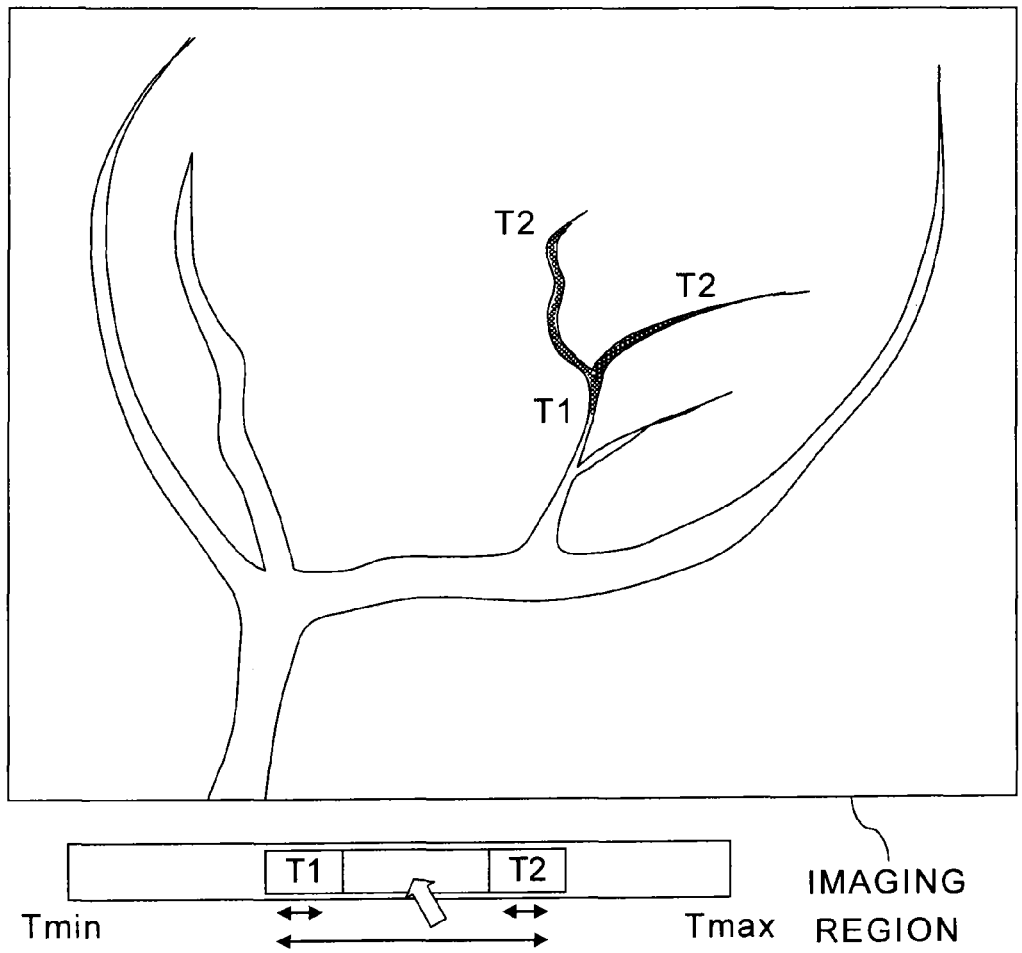
FIG. 10 is a view for explaining the second example of method of setting a focused region, for which parametric image data is generated, in terms of time.

FIG. 10 is a view for explaining the second example of method of setting a focused region, for which parametric image data is generated, in terms of time.

The range of arrival time phases of a contrast agent for specifying pixel positions for which parametric image data are generated can also be designated directly as a range of time phases instead of positions. In other words, a time range specified by operations of an input device can be set as a focused time for which parametric image data are generated.

As a specific example, a scroll bar for arbitrarily adjusting the lower limit T1 of time phases, the upper limit T2 of the time phases, and a range of the time phases, for limiting arrival time phases of the contrast agent can be prepared as a graphical user interface (GUI) as shown in FIG. 10.

In the example shown in FIG. 10, the lower limit T1 of time phases can be adjusted by sliding the scroll bar, for adjusting the lower limit T1 of the time phases, by operating an input device. Similarly, the upper limit T2 of the time phases can be adjusted by sliding the scroll bar, for adjusting the upper limit T2 of the time phases, by operating an input device. Furthermore, the time range itself, set as a time phase period between the lower limit T1 of the time phases and the upper limit T2 of the time phases, can be adjusted in the time phase direction by sliding the scroll bar.

Thus, positions where times, at which concentrations of a contrast agent become a specific condition such as the maximum values, are within a specific time range, inside an imaging region where is an image acquisition area of X-ray contrast image data can be set as a focused range for which parametric image data are generated. In other words, a focused region can be set indirectly as a focused time which is a part of an acquisition time of time series frames of X-ray contrast image data.

Then, a period between respective times at which concentrations of a contrast agent at different two points, on a blood vessel, designated by operations of an input device through a reference image, such as a DSA image, of an imaging region of X-ray contrast image data become a specific condition such as the maximum values can be set to a specific time range for determining a focused range for which parametric image data are generated, as exemplified in FIG. 9. Alternatively, a time range directly designated by operations of an input device can also be set as a specific time range, as exemplified in FIG. 10.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the first embodiment can be combined with the second embodiment. Specifically, a focused range for which parametric image data are generated can be set inside an imaging region of X-ray contrast image data in terms of space and time. In this case, positions, which lie in a focused region set spatially on a reference image such as a DSA image, at which times when concentrations of a contrast agent become a specific condition such as the maximum values are within a specific time range set separately, are a target for which parametric image data are generated. In this case as well, an exclusion of blood vessels, which are not focused, from a focused range can be performed by tracking of a designated blood vessel.

What is claimed is:

1. A medical image processing apparatus comprising:
an image data reception part configured to receive at least one of X-ray contrast image data and subtraction image data, of an imaging region including blood vessels of an object, the subtraction image data being generated by subtraction processing between the X-ray contrast image data and non-contrast X-ray image data;
a range setting part configured to set a target range in the received X-ray contrast image data or the received subtraction image data; and
a blood vessel image generation part configured to derive time changes in concentrations of a contrast agent based on the received X-ray contrast image data or the received subtraction image data, and generate blood vessel image data having pixel values corresponding to times, at which concentrations of the contrast agent become a specific condition, within the target range and pixel values corresponding to concentrations of the contrast agent outside the target range.

2. A medical image processing apparatus of claim 1, wherein said blood vessel image generation part is configured to generate the blood vessel image data according to time changes in concentrations, of the contrast agent, in a period when the contrast agent is flowing inside the target range, the period lying between an injection period when the contrast agent is being injected into the object, the blood vessel image data being generated based on the X-ray contrast image data or the subtraction image data corresponding to the injection period.

3. A medical image processing apparatus of claim 1, wherein said blood vessel image generation part is configured to make a color scale in which colors have been related to a range of the times at which the concentrations of the contrast agent in the target range become the specific condition, and generate blood vessel image data, having color pixel values, according to the color scale.

4. A medical image processing apparatus of claim 3, wherein said blood vessel image generation part is configured to make the color scale corresponding to the target range by contracting an initial color scale in a time direction, the initial color scale having initial colors related to a range of times at which concentrations of the contrast agent in the imaging region become the specific condition.

5. A medical image processing apparatus of claim 3, wherein said blood vessel image generation part is configured to make a color scale in which a color variation is periodically repeated multiple times, and generate the blood vessel image data according to the color scale, the color scale being related with the range of the times at which the concentrations of the contrast agent in the target range become the specific condition.

6. A medical image processing apparatus of claim 3, wherein said blood vessel image generation part is configured to make color scales between which the colors, related to the range of the times at which the concentrations of the contrast agent in the target range become the specific condition, vary temporally, and generate the blood vessel image data as a moving image whose colors vary temporally according to the color scales.

7. A medical image processing apparatus of claim 1, further comprising:
a display part configured to superimpose and display X-ray contrast image data or subtraction image data in the target range of the blood vessel image data, the X-ray contrast image data or the subtraction image data in the target range corresponding to the blood vessel image data in the target range.

8. A medical image processing apparatus of claim 1, wherein said range setting part is configured to set a region as the target range, the region being designated by an operation of an input device.

9. A medical image processing apparatus of claim 1, wherein said range setting part is configured to set an area as the target range, the area lying in the imaging region, times at which concentrations of the contrast agent become the specific condition being within a specific time range in the area.

10. A medical image processing apparatus of claim 9, wherein said range setting part is configured to set the specific time range as a period between times at which concentrations of the contrast agent at different two points on a blood vessel become the specific condition, as, the two points being designated by an operation of an input device through a reference image in the imaging region.

11. A medical image processing apparatus of claim 9, wherein said range setting part is configured to set the specific time range as a time range designated by an operation of an input device.

12. A medical image processing apparatus of claim 1, wherein said range setting part is configured to detect a continuous target blood vessel region by tracking a blood vessel at a position in the target range, and remove a blood vessel region, unconnected with the target blood vessel region, from the target range, the position being designated by an operation of an input device.

13. A medical image processing apparatus of claim 12, wherein said range setting part is configured to track the blood vessel by first threshold processing of maximum concentrations of the contrast agent in the target range and second threshold processing of differences in times, at which concentrations of the contrast agent become the specific condition, between adjacent pixel positions in the target range.

14. A medical image processing apparatus of claim 1, wherein said blood vessel image generation part is configured to generate first blood vessel image data and second blood vessel image data individually in order to be able to display the first blood vessel image data and the second blood vessel image data in parallel, the first blood vessel image data having the pixel values corresponding to the times at which the concentrations of the contrast agent in the target range become the specific condition, the second blood vessel image data having pixel values corresponding to concentrations of the contrast agent in the imaging region.

15. An X-ray diagnostic apparatus comprising:
an imaging system configured to acquire at least X-ray contrast image data of an imaging region including blood vessels of an object;
a range setting part configured to set a target range in the X-ray contrast image data or subtraction image data generated by subtraction processing between the X-ray contrast image data and non-contrast X-ray image data; and
a blood vessel image generation part configured to derive time changes in concentrations of a contrast agent based on the X-ray contrast image data or the subtraction image data, and generate blood vessel image data having pixel values corresponding to times, at which concentrations of the contrast agent become a specific condition, within the target range and pixel values corresponding to concentrations of the contrast agent outside the target range.

16. A medical image processing method comprising:
receiving at least one of X-ray contrast image data and subtraction image data, of an imaging region including blood vessels of an object, the subtraction image data being generated by subtraction processing between the X-ray contrast image data and non-contrast X-ray image data;
setting a target range in the received X-ray contrast image data or the received subtraction image data; and
deriving time changes in concentrations of a contrast agent based on the received X-ray contrast image data or the received subtraction image data, and generating blood vessel image data having pixel values corresponding to times, at which concentrations of the contrast agent become a specific condition, within the target range and pixel values corresponding to concentrations of the contrast agent outside the target range.

* * * * *

UNITED STATES PATENT AND TRADEMARK OFFICE
CERTIFICATE OF CORRECTION

PATENT NO. : 9,433,392 B2  
APPLICATION NO. : 14/551253  
DATED : September 6, 2016  
INVENTOR(S) : Satoru Ohishi Page 1 of 1

It is certified that error appears in the above-identified patent and that said Letters Patent is hereby corrected as shown below:

On the Title Page

Item (71), the Applicant's information is incorrect. Item (71) should read:

-- (71) Applicant: Toshiba Medical Systems Corporation, Otawara-shi (JP) --

Signed and Sealed this  
Sixth Day of March, 2018

Andrei Iancu  
*Director of the United States Patent and Trademark Office*